United States Patent
Cushman

(10) Patent No.: US 8,889,372 B2
(45) Date of Patent: Nov. 18, 2014

(54) ADAPTIVE CONTROL OF MICROBIAL POPULATIONS

(71) Applicant: Michael Cushman, Guanacaste (CR)

(72) Inventor: Michael Cushman, Guanacaste (CR)

(73) Assignee: Michael Cushman, Playas El Coco, Guanacaste (CR)

( * ) Notice: Subject to any disclaimer, the term of this patent is extended or adjusted under 35 U.S.C. 154(b) by 0 days.

(21) Appl. No.: 13/871,292

(22) Filed: Apr. 26, 2013

(65) Prior Publication Data

US 2013/0288288 A1    Oct. 31, 2013

Related U.S. Application Data

(60) Provisional application No. 61/639,237, filed on Apr. 27, 2012.

(51) Int. Cl.

| | | |
|---|---|---|
| *A61K 36/05* | (2006.01) | |
| *C12N 1/00* | (2006.01) | |
| *C12N 1/38* | (2006.01) | |
| *C12N 5/00* | (2006.01) | |
| *C12P 7/06* | (2006.01) | |
| *C12Q 1/02* | (2006.01) | |
| *C12N 1/12* | (2006.01) | |
| *C12M 1/36* | (2006.01) | |
| *A01G 7/00* | (2006.01) | |
| *A61K 36/02* | (2006.01) | |

(52) U.S. Cl.
CPC ...................................... *C12N 1/38* (2013.01)
USPC ............ 435/41; 435/161; 435/29; 435/257.1; 435/286.1; 47/1.4

(58) Field of Classification Search
None
See application file for complete search history.

(56) References Cited

U.S. PATENT DOCUMENTS

| 7,968,321 B1 * | 6/2011 | Green et al. ................... 435/161 |
| 8,507,253 B2 * | 8/2013 | Berzin ........................ 435/257.1 |
| 2008/0161413 A1 * | 7/2008 | Okada ............................ 514/691 |
| 2009/0011492 A1 * | 1/2009 | Berzin ........................ 435/257.1 |
| 2011/0151507 A1 * | 6/2011 | Van Walsem et al. .......... 435/41 |

FOREIGN PATENT DOCUMENTS

WO    WO 2010068288 A2 *    6/2010

OTHER PUBLICATIONS

Jang, J-S; Cho, Y; Jeong G-T; Kim, S-K "Optimization of Saccharification and Ethanol Production by Simultaneous Saccharification and Fermentation (SSF) from Seaweed, *Saccharina japonica*" Bioprocess Biosyst. Eng., 2012 (published online Sep. 15, 2011), 35, pp. 11-18.*

Kim, W; Park, JM; Gim, GH, Jeong, S-H; Kang, CM; Kim, D-J; Kim SW "Optimization of Culture Conditions and Comparison of Biomass Productivity of Three Green Algae" Bioprocess Biosyst. Eng., 2012 (published online Sep. 10, 2011), 35, pp. 19-27.*

Sheehan, et al. "A Look Back at the U.S. Department of Energy's Aquatic Species Program: Biodiesel from Algae," National Renewable Energy Laboratory, NREL/TP-580-24190, Jul. 1998, 328 pp.*

* cited by examiner

*Primary Examiner* — Jon P Weber
*Assistant Examiner* — Aaron J Kosar
(74) *Attorney, Agent, or Firm* — Ward and Smith, P.A.

(57) ABSTRACT

The presently disclosed subject matter provides real-time adaptive manipulations of conditions in a bioreactor to optimize biochemical reactions occurring within the bioreactor. Optimization of a bioreactor does not need to be performed in small-scale, but real-time adaptive manipulations can occur in a bioreactor while the bioreactor is being used.

9 Claims, No Drawings

ADAPTIVE CONTROL OF MICROBIAL POPULATIONS

CROSS-REFERENCE TO RELATED APPLICATIONS

This application claims the benefit of U.S. Provisional Application No. 61/639,237, filed Apr. 27, 2012; which is incorporated herein by reference in its entirety.

BACKGROUND

Bioreactors are typically containers used to hold organisms for the purpose of harnessing their natural biochemical processes and are used for many purposes. Microbial reactors, which hold microorganisms, such as microalgae, bacteria, yeasts, and the like, are used to produce various products, including, but not limited to, foods, feeds, nutritional products, energy supplies, such as biodiesel, hydrogen, and alcohols, pharmaceuticals, and specialty chemicals. They also are used extensively for environmental control and remediation and waste treatment of many types.

Several types of large-scale bioreactors currently are in use. In a batch bioreactor, all of the stock materials, reactants, nutrients, and the like, are added at once to a controlled environment and the biochemical reactions are allowed to proceed. In a continuous flow bioreactor, materials constantly flow through the bioreactor. In either case, bioreactors may be enclosed, open or a combination of the two. In most cases, it is recognized that the performance of these reactors can be improved to produce more product or more efficient remediation or waste treatment.

SUMMARY

The presently disclosed subject matter provides methods for improving the productivity of a bioreactor. More particularly, in one aspect, the methods improve the productivity of a biochemical reaction in a bioreactor in real-time. The presently disclosed methods comprise changing a condition in a bioreactor and measuring the change in productivity of a biochemical reaction in the bioreactor, while the biochemical reaction is still taking place.

In one particular aspect, the methods improve the productivity of a biochemical reaction involving at least one microorganism in a bioreactor in real-time. The presently disclosed methods comprise changing a condition in a bioreactor, measuring a change in productivity in the bioreactor, wherein the biochemical reaction is still taking place in the bioreactor, and wherein improving the productivity of the biochemical reaction results from a change in the genetic code, a change in the expression of at least one gene, a change in the activity of at least one gene product, a change in the cell wall permeability, and/or a change in the cell membrane permeability of at least one microorganism involved in the biochemical reaction.

Certain aspects of the presently disclosed subject matter having been stated hereinabove, which are addressed in whole or in part by the presently disclosed subject matter, other aspects will become evident as the description proceeds when taken in connection with the accompanying Example as best described herein below.

DETAILED DESCRIPTION

The presently disclosed subject matter now will be described more fully hereinafter, in which some, but not all embodiments of the presently disclosed subject matter are shown. The presently disclosed subject matter may be embodied in many different forms and should not be construed as limited to the embodiments set forth herein; rather, these embodiments are provided so that this disclosure will satisfy applicable legal requirements. Indeed, many modifications and other embodiments of the presently disclosed subject matter set forth herein will come to mind to one skilled in the art to which the presently disclosed subject matter pertains having the benefit of the teachings presented in the foregoing descriptions. Therefore, it is to be understood that the presently disclosed subject matter is not to be limited to the specific embodiments disclosed and that modifications and other embodiments are intended to be included within the scope of the appended claims.

The use of bioreactors, or bioreactors coupled with other chemical or physical devices, is becoming increasingly important in the production of materials and in the removal or remediation of environmental materials. Many advances in the design and control of such reactors have been made. Space-time yields have steadily been increased through the use of engineering and biological principles.

As defined herein, a "bioreactor" includes a container, which holds an organism or a part of an organism, for the purpose of harnessing its natural biochemical processes. Typically, the organism or part of an organism in a bioreactor is one or more microbes, one or more animal products, including one or more animal cells, or one or more plant cells.

A "biochemical reaction" as defined herein is a reaction in which two or more reactants interact to produce at least one product and wherein the reaction is aided by a living organism or a part of a living organism, such as a cell culture or an enzyme from an organism.

The presently disclosed subject matter calls for real-time measurement and change of various parameters as the biochemical reaction proceeds. In continuous flow bioreactors, certain parameters, such as pH, temperature, substrate feed rate, and the like, are controlled based on predetermined values. The methods of the presently disclosed subject matter provide for a change in values of parameters in real-time rather than trying to maintain predetermined values or predict optimal values before the start of the biochemical reaction. These methods allow for the optimal conditions for a biochemical reaction to be determined as the reaction proceeds. As such, the presently disclosed subject matter provides real-time adaptive manipulations of variables in a bioreactor.

"Adaptive manipulation" means that a variable or variables can be changed in the bioreactor, the results can be monitored, and then variables can be changed again while the reaction(s) in the bioreactor is still proceeding. These methods can be performed multiple times during the processing in the bioreactor such that the conditions in the bioreactor are adapted toward more optimal conditions for the target biochemical reactions.

In contrast, in the current state of the art, conditions for biochemical reactions in a batch bioreactor typically are not changed in a bioreactor after the reactor starts running, but are determined in small-scale experiments before a bioreactor is prepared. The performance of an organism or a cell culture, however, can be very different in a one-liter flask, a 10-liter laboratory reactor, and a 10,000-liter large-scale bioreactor. Such differences arise because scale-up of a living culture or cells tends to change the conditions for optimal growth of the culture. Variables, such as surface-to-volume ratio of the liquid culture, the amount of time that the cells are in the bioreactor, the amount of oxygen available in a large volume, and the like, change as volumes of the culture increase. Therefore, trying to determine the optimal conditions in a bioreactor before the biochemical reaction(s) is initiated may not be accurate. As such, the methods of the presently disclosed subject matter allow optimal conditions to be determined in a bioreactor in real-time. By "real-time" it is meant that the variables in a bioreactor are changed while the relevant biochemical reaction(s) are taking place in the bioreactor.

In one embodiment, the presently disclosed subject matter provides methods to optimize biochemical reactions in a large-scale bioreactor, such as a bioreactor that has a capacity of about 500 or more liters. In another embodiment, the methods are applicable to smaller bioreactors, such as bioreactors that have a capacity of less than about 500 liters. These methods obviate the need to determine how to transition from smaller-scale bioreactors to the conditions needed for a larger bioreactor.

The presently disclosed subject matter provides methods for improving the productivity of bioreactors in real-time. In one embodiment, the presently disclosed methods improve the productivity of a bioreactor by increasing the productivity of at least one biochemical reaction in the bioreactor in real-time. In one embodiment, the method comprises changing a condition in a bioreactor and measuring the change in productivity of a biochemical reaction involving at least one microorganism in the bioreactor while the biochemical reaction is still taking place in the bioreactor, wherein improving the productivity of the biochemical reaction results from a change in the genetic code, a change in the expression of at least one gene, a change in the activity of at least one gene product, a change in the cell wall permeability, and/or a change in the cell membrane permeability of at least one microorganism involved in the biochemical reaction. Other physical parameters of a microorganism may result in a change in productivity of a biochemical reaction in a bioreactor.

Changing the conditions in a bioreactor according to the methods of the presently disclosed subject matter is expected to significantly increase the productivity of the bioreactor, such as on the order of 10 fold or higher. These conditions include, but are not limited to, pH, one or more nutrients added, temperature, pressure, gas partial pressure, light (wavelength, intensity, duration, and the like), ultrasonic input, one or more electrical signals added, one or more metals added and the like. The conditions may be ones that are not common for the target biochemical reaction or microorganism. For example, in some cases, a pH significantly outside of the pH thought to be optimal for a microorganism may result in prolific growth of the microorganism in a bioreactor. As another example, a nutrient not thought to be needed by the microorganism, such as a metal, may result in increased productivity of the microorganism in a bioreactor.

The bioreactor can hold microorganisms, such as microalgae, bacteria, anaerobic bacteria, fungi (e.g., yeast), protozoa, viruses, and the like, to perform the target biochemical processes. The bioreactor also can contain cell cultures, such as mammalian cell cultures (e.g., CHO cells) or plant cell cultures. Multiple types of organisms may be required to perform the necessary biochemical processes. The bioreactor also or alternatively can hold parts of an organism, such as enzymes extracted from a living organism, to aid in performing the biochemical processes of interest. Therefore, the biochemical reaction may occur in an organism, such as in a microorganism (e.g., microalgae), in a cell culture system, or by using components of a cell.

The conditions in the bioreactor can be adjusted manually or by a preprogrammed set of variations or adjusted by a computer program, such as a neural network, a Partial Least Squares algorithm or any other program used for control and learning purposes. The adjustments in one or more conditions can be made iteratively, sequentially, or simultaneously.

The bioreactor used in the methods of the presently disclosed subject matter is typically a continuous flow bioreactor rather than a batch bioreactor so that conditions can be changed while the biochemical processes are carried out. Once more productive conditions are determined, they may be applied to a batch reactor, as well. With an accurate real-time measurement and a process response having a short time constant, adaptations can be effected in a batch mode. The bioreactor can be a photobioreactor, a fermentation device, a chemostat, a waste treatment device, or any other bioreactor that can be used for the methods of the presently disclosed subject matter.

Changes in the productivity in the bioreactor or of the biochemical reactions occurring within the bioreactor can mean an increase of at least one product of the biochemical reaction, a decrease in at least one initial substrate added to the bioreactor, faster reaction times, improved specificity of the biochemical reaction, an increase in biomass of the microorganism responsible for the reaction, or any other pertinent performance characteristic. As a person with ordinary skill in the art would appreciate, the type of measurement to determine a change in productivity in the bioreactor will depend on the relevant biochemical processes taking place in the bioreactor.

The change in productivity may occur rapidly, such as in a matter of seconds or minutes, or may occur during a longer period of time, such as during days or months depending on the reaction time of the biochemical reaction taking place and other variables. The number of times that adaptive manipulation of variables in the bioreactor is required also will vary depending on the unique circumstances in each bioreactor, such as how close to optimal conditions the initial conditions were before the biochemical reaction was started. Adaptive manipulation may be required only once for optimal conditions to be set in the bioreactor, or adaptive manipulation may be required more than once, such as 5, 10, 20, 50, 100, 1000, or more times per hour.

The cause of change in productivity may be determined, although this determination is not a requirement of the methods of the presently disclosed subject matter. The cause may be measured by, but is not limited to, assaying for a change in the genetic code using DNA sequencing and the like, assaying for a change in gene expression using RNA expression analyses, Northern blot analyses, reverse transcription quantitative PCR, and the like, and/or assaying for the amount or activity of a gene product using protein activity assays, immunohistochemical assays, Western blot analyses, ELISA assays, and the like. As another example, fluorescent proteins, such as green fluorescent protein or bioluminescent proteins, such as luciferase, may be used to illuminate cells in a bioreactor. A change in productivity from the activation or repression of an entire biochemical pathway or part of a pathway also may be determined using, but not limited to, high-throughput gene expression analyses, such as DNA microarrays and other methods to analyze the transcriptome or proteome of a microorganism.

The presently disclosed methods involve chosen or random variation of any or all system inputs while following the resulting effect on the chosen parameter or parameters of interest. Therefore, multiple input conditions or variables can be varied or changed in accordance with the direct measurement of the desired product or effect and new and unknown interactions can be discovered and exploited. It is expected that random real-time adaptive manipulation of conditions in a bioreactor might result in unexpected higher productivity of a bioreactor. By measuring the effects of these conditions or variations, a given system can be improved for the chosen parameter. When improvements are realized, investigation into the responsible pathway and gene activities can be initiated. For instance, if a given pathway is observed or thought to be involved in an improvement, then a real-time reporter gene or protein might be added to that pathway so that it can be more carefully explored.

The presently disclosed subject matter provides methods for selecting for a desired molecular level response by the application of real-time measurements coupled with the controlled manipulation of system inputs in a bioreactor. The presently disclosed methods provide an alternative to the rapidly growing field of genetic manipulation or genetically modified organisms. Without wishing to be bound to any one particular theory, it is believed that the presently disclosed methods preferentially select particular genes and genetic pathways by monitoring the performance of the system, while controlling various system inputs with feedback to the control based on continued performance. While the use of this approach may lead to preferential gene expression, no new genes are being introduced.

On a molecular level, certain pathways and how they respond to external stimuli are incorporated into evolutionary adaptation. It is generally accepted that this process occurs over long periods of time and many generations. In contrast, the presently disclosed methods include molecular/pathway adaptations that occur in response to external stimuli. Said another way, the presently disclosed methods, in some embodiments, include selecting or turning on a particular pathway in response to external stimuli.

Knowledge of the effects of various parameters in the environment on the performance of biological systems has steadily improved. For instance, it is now known that the photosynthetic response of chlorophyll is subject to photo inhibition if more light is presented than the maximum that can be used. As another example, certain yeasts differentially express particular subunits of cytochrome oxidase depending on oxygen levels in the environment. Also, certain heat shock genes respond to heat or oxygen deprivation. Similar observations on the role of very narrow ranges of concentration of individual nutrients on the overall growth rate of organisms also have been made.

As another example, *Haemmatococcus pluvialis* can change from free swimming microalgae into an encysted organism that can produce astaxanthin, a desired product. This process comprises a series of environmental challenges that induce a major change in the biochemical pathways induced by the organism (Olaizola, 2003).

Also, Kim et al. described the laboratory optimization of three species of green algae for biomass productivity. They used a Response Surface Methodology to optimize three inputs, pH, nitrogen and phosphate concentrations, for maximum growth. They discovered that at a given $CO_2$ concentration, each species needed a different profile of these inputs and that the nitrogen source was different for the best performance of one of the species. By optimizing these three parameters, they determined that one of the species would be better than the other two for maximum growth of biomass (Kim et al., 2012).

Melis et al. showed that by sulfur deprivation a pathway can be blocked and result in an increased production of $H_2$ by *Chlamydonomas reinhartdii*. Under these conditions, $H_2$ production, which would normally be blocked by $O_2$ production, was favored (Melis et al., 2007).

Carrieri et al. have shown that inducing hypoionic stress through sodium cycling can improve the production of acetate, ethanol, and formate in *Spirulina maxima* (Carrieri et al., 2010). Increases of over 100 fold were achieved for ethanol production. The increase of ethanol production and its secretion have a direct impact on biofuel production. Knowledge of the effects of electrical signals that can be pulsed or steady on the throughput of pathways or the permeability of cell walls and membranes also has been advanced. For example, electrical pulses have been used in bioreactors or post-bioreactor processes to extract proteins (Teissie et al., 2002) or oils (Origin Oil, Inc.) from microbial populations.

Further, the photo inhibition of algal cells can be overcome by the use of specific wavelengths and durations of pulsed LEDs (Gordon and Polle, 2007). As another example, the production of ethanol by *Saccharomyces cerevisiae* can be enhanced with the use of ultrasonic irradiation (Jomdecha and Prateepasen, 2011). All of these effects have been demonstrated, but are often not fully understood.

The examples discussed hereinabove of the effect of various conditions on the performance of biological systems can be used in the methods of the presently disclosed subject matter to increase or optimize the productivity of biochemical reactions in a bioreactor. Of course, there are many other conditions that can be optimized in a bioreactor using the methods of the presently disclosed subject matter. Again, without wishing to be bound to any one particular theory, the observed changes in the bioreactor productivity can be a result of changes in the genetic code, changes in the expression level of the genes, changes in the activity of a gene product, changes in the cell wall permeability, changes in the cell membrane permeability or a combination thereof, although any of these changes need not occur for an increase in the productivity of a bioreactor to be observed in response to adjusting one or more conditions of the process.

EXAMPLE

The following Example has been included to provide guidance to one of ordinary skill in the art for practicing representative embodiments of the presently disclosed subject matter. In light of the present disclosure and the general level of skill in the art, those of skill can appreciate that the following Example is intended to be exemplary only and that numerous changes, modifications, and alterations can be employed without departing from the scope of the presently disclosed subject matter.

A culture of *Haematococcus pluvialis* is added to a stirred photobioreactor. Stirring is continuous and light is provided by fluorescent fixtures. The pH is adjusted and $CO_2$ is continuously supplied. An in situ probe is inserted in the reactor, which provides a readout of total cell density with time in the reactor. Temperature is controlled and a basic culture medium is supplied. After several runs are performed, a baseline of growth vs. time is established.

Various metal solutions are added at different concentrations and the growth profile is compared to the baseline case. One metal is found to greatly influence the growth rate while the other metals do not. That metal is added in a fresh reaction over time with increasing concentration. A very narrow range of concentration of that metal is found to be optimal. By monitoring and controlling that metal concentration in that narrow range, a significant increase in biomass is produced over the same time as the baseline case.

Alternatively, the bioreactor is modified to be flow-through with regard to the medium. By the use of metering pumps, the various metal concentrations are randomly changed with time in the reactor. The changes are step functions but gradual enough such that a growth rate is determined for each condition. These rates are examined versus the various concentrations and it is discovered that only the one metal is important and that it is confined to very narrow range.

As a second alternative, the same flow-through reactor is used, but using the output of the probe as a guide, an algorithm varies the metal concentrations and randomly walks through the concentration space until it finds the maximum growth rate. The outcome is the same—one metal in a very narrow concentration range. In this case, however, it would have been determined in a very short time if there were interactions between the various inputs (metal concentrations). Other inputs, such as temperature, $CO_2$ partial pressure, or any other variable could be added.

REFERENCES

All publications, patent applications, patents, and other references mentioned in the specification are indicative of the level of those skilled in the art to which the presently disclosed subject matter pertains. All publications, patent applications, patents, and other references are herein incorporated by reference to the same extent as if each individual publication, patent application, patent, and other reference was specifically and individually indicated to be incorporated by reference. It will be understood that, although a number of patent applications, patents, and other references are referred to herein, such reference does not constitute an admission that any of these documents forms part of the common general knowledge in the art.

Carrieri, D.; Momot, D.; Brasg, I. A.; Ananyev, G.; Lenz, O.; Bryant, D. A.; Dismukes, G. C. Boosting autofermentation rates and product yields with sodium stress cycling: application to production of renewable fuels by cyanobacteria. 2010, 76(19), 6455-62.

Gordon, J. M. and Polle, J. E. Ultrahigh bioproductivity from algae. Appl. Microbiol. Biotechnol., 2007, 76(5), 969-975.

Jomdecha, C. and Prateepasen, A. Effects of pulse ultrasonic irradiation on the lag phase of *Saccharomyces cerevisiae* growth. Lett. Appl. Microbiol., 2011, 52(1), 62-69.

Kim, W.; Park, J. M.; Gim, G. H.; Jeong, S. H.; Kang, C. M.; Kim, D. J.; Kim S. W. Optimization of culture conditions and comparison of biomass productivity of three green algae. Bioprocess. Biosyst. Eng., 2012, 35(1-2), 19-27.

Melis, A.; Seibert, M., Ghirardi, M. L. Hydrogen fuel production by transgenic microalgae. Adv. Exp. Med. Biol., 2007, 616, 110-121.

Olaizola, M. Commercial development of microalgal biotechnology: from the test tube to the marketplace. Biomol. Eng., 2003, 20(4-6), 459-466.

Teisie, J.; Eynard, N.; Vernhes, M. C.; Benichou, A.; Ganeva, V.; Galutzov, B.; Cabanes, P. A. Recent biotechnological developments of electropulsation. A prospective view. Bioelectrochemistry, 2002, 55(1-2), 107-112.

Although the foregoing subject matter has been described in some detail by way of illustration and example for purposes of clarity of understanding, it will be understood by those skilled in the art that certain changes and modifications can be practiced within the scope of the appended claims.

That which is claimed:

1. A method for increasing the productivity of a biochemical reaction involving at least one microorganism in a bioreactor in real-time, the method comprising:
    (a) in a bioreactor providing a culture of at least one microorganism under conditions whereby a biochemical reaction to which the at least one microorganism is involved is taking place;
    (b) changing in real-time at least one of the conditions in the bioreactor, wherein the at least one condition is selected from the group consisting of pH, temperature, pressure, gas partial pressure, light, ultrasonic input, and an amount of one or more nutrient, one or more metal, and/or one or more electric signal, and combinations thereof;
    (c) measuring in real-time a change in productivity in the biochemical reaction wherein the change in productivity is selected from the group consisting of an increased amount of at least one product of the biochemical reaction, a decreased amount of at least one initial substrate of the biochemical reaction, a faster reaction time of the biochemical reaction, an improved specificity of the biochemical reaction, and an increase in the microorganism's culture biomass density; and wherein said real-time changing and measuring provides increasing the productivity of the biochemical reaction to a maximum of said productivity in a time period that is shorter than a reference process which is changing and/or measuring therein are not real-time changing and/or measuring.

2. The method of claim 1, wherein the bioreactor is a large-scale bioreactor having a capacity of about 500 liters or more.

3. The method of claim 1, wherein the change in productivity is measured by said increased amount of at least one product of the biochemical reaction.

4. The method of claim 1, wherein the change in productivity is measured by said decreased amount of at least one initial substrate of the biochemical reaction.

5. The method of claim 1, wherein the change in productivity comprises a measurement selected from the group consisting of a faster reaction time of the biochemical reaction, an improved specificity of the biochemical reaction, and an increase in the microorganism's culture biomass density.

6. The method of claim 1, wherein multiple of said conditions are changed.

7. The method of claim 1, wherein the real-time changing comprises changing said at least one of the conditions using a computer program.

8. The method of claim 1, wherein the microorganism is a microalgae.

9. The method of claim 8, wherein the microalgae is *Haematococcus pluvialis*.

* * * * *